United States Patent [19]
Taha et al.

[11] Patent Number: 5,840,323
[45] Date of Patent: Nov. 24, 1998

[54] AGGLOMERATED CARRIER CONTAINING A SOIL RELEASE POLYMER AND AN ANTIBACTERIAL AGENT FOR LAUNDRY APPLICATIONS

[75] Inventors: Riad Ahmed Taha, Spotswood; Patrick J. Getty, Metuchen, both of N.J.

[73] Assignee: Colgate-Palmolive Co., New York, N.Y.

[21] Appl. No.: 918,933

[22] Filed: Aug. 25, 1997

[51] Int. Cl.$^6$ ...................................... A01N 25/10
[52] U.S. Cl. ........................ 424/405; 424/404; 424/78.17
[58] Field of Search .................... 424/405, 402, 424/404, 419, 486, 78.17, 78.18; 523/122

[56] References Cited

U.S. PATENT DOCUMENTS

| | | | |
|---|---|---|---|
| 3,962,152 | 6/1976 | Nicol et al. | 252/551 |
| 4,803,256 | 2/1989 | Luckenbach | 525/420 |

OTHER PUBLICATIONS

Miyazaki et al., *Chemical Abstracts*, vol. 127, #52,144, Jul. 28, 1997.
Yamakawa, *Chemical Abstracts*, vol. 123, #35,842, 1996.

*Primary Examiner*—Neil S. Levy
*Attorney, Agent, or Firm*—Bernard Lieberman

[57] ABSTRACT

A particulate agglomerated carrier is described which is suitable for use in admixture with a laundry detergent composition and which is capable of depositing an effective amount of an antibacterial agent on laundered fabrics and for providing an effective amount of same in the wash solution. The carrier is an agglomerate of (i) a soil release copolymer of polyethylene terephthalate (PET) and polyoxyethylene terephthalate (POET); and (ii) an antibacterial agent.

Also, described is a laundry detergent composition containing such agglomerated carrier and process for depositing an effective amount of an antibacterial agent on laundered fabrics and for providing such antibacterial agent in the wash solution.

16 Claims, No Drawings

AGGLOMERATED CARRIER CONTAINING A SOIL RELEASE POLYMER AND AN ANTIBACTERIAL AGENT FOR LAUNDRY APPLICATIONS

FIELD OF THE INVENTION

This invention relates to agglomerated carrier particles containing a soil release polymer and an antibacterial agent. More particularly, it relates to the use of such agglomerated particles as a component of a laundry detergent composition or as an additive to the wash solution for depositing an effective amount of antibacterial agent on laundered fabrics and for providing an effective amount of such antibacterial agent in the wash solution.

DESCRIPTION OF RELATED ART

The combination of an antibacterial agent with a particulate carrier material to provide an antibacterial composition capable of sterilizing or inhibiting the growth of bacteria in a liquid or on a solid surface is extensively described in the patent literature. In U.S. Pat. No. 5,011,602 there is described what is referred to as an antibacterial material for water which is used to sterilize water and which is comprised of an antibacterial agent bound or adsorbed on a carrier. In U.S. Pat. No. 5,478,563 there is described "an easily condensable antibacterial agent" which is adsorbed on a carrier such as zeolite or clay among numerous other listed materials, and the resulting particulate carrier then blended with a described plastic resin to provide an antibacterial polyacetal resin composition.

The use of DCMX (dichloro meta xylenol) as a bacteriostat on a carrier is described in U.S. Pat. No. 4,494,482 to provide an animal litter product intended to control odor development.

Soil release polymers, and in particular, those commonly referred to as PET-POET copolymers (polyethylene terephthalate-polyoxyethylene terephthalate) have been widely suggested as components of detergent compositions. U.S. Pat. Nos. 4,569,772 and 4,571,303 to Ciallella describe nonionic detergent compositions containing stabilized PET-POET copolymers as soil release agents.

U.S. Pat. No. 5,026,400 to Holland et al describes compositions containing narrow range ethoxylate nonionic detergents in combination with PET-POET copolymers and builders.

U.S. Pat. No. 5,496,490 to Beagle et al. discloses particulate laundry detergent compositions which contain a PET-POET soil release polymer in combination with lipase enzyme to provide enhanced removal of oily soils.

SUMMARY OF THE INVENTION

In accordance with the present invention there is provided a particulate agglomerated carrier which is an agglomerate of (i) a soil release copolymer of polyethylene terephthalate (PET) and polyoxyethylene terephthalate (POET); and (ii) an antibacterial agent, which carrier is suitable for use in admixture with a laundry detergent composition or as an additive to a wash solution separate from any detergent composition, and which carrier is capable of depositing an effective amount of said antibacterial agent on laundered fabrics, said carrier being comprised of (a) particles of said soil release copolymer; and
(b) an antibacterial agent which is normally solid at ambient temperature, wherein said particles of soil release copolymer are agglomerated at a temperature above ambient with a melt of said antibacterial agent to form an agglomerated mixture which is reduced in size to the range of particle size desired for said particulate carrier.

In accordance with the process aspect of the invention antibacterial activity is provided to laundered fabrics by contacting such fabrics during a laundering operation with wash water or rinse water containing dispersed therein the above-defined particulate agglomerated carrier.

The process of the invention can be conveniently carried out in a washing machine during laundering or by contact of the fabrics with a wash solution or rinse solution during hand washing.

In a preferred embodiment of the invention the soil release copolymer of PET and POET has a molecular weight in the range of from about 5,000 to 50,000, a range of about 9,000 to 20,000 being especially preferred.

The term "antibacterial agent" as used herein refers to materials which prevent or inhibit the growth of bacteria on an inanimate surface.

Among the known antibacterial agents which are suitable for the present invention are phenolic and xylenol antibacterial agents. Two are particularly preferred: PCMX (para chlorometa xylenol) and triclosan (2,4,4'-trichloro-2'-hydroxy diphenyl ether). These are normally solid at room temperature and have melting points of about 115° C. for PCMX and about 50° C. for triclosan.

Other useful antibacterial agents include 3,4,4'-trichloro carbanilide, DTBBP (2,t-butyl-4-cyclohexylphenol) and other suitable antibacterial compounds containing phenol groups. Also useful herein are oxidants such as sodium perborate, activated perborate, percarbonate and the like.

Less preferred for the present invention are those antibacterial agents such as quaternary ammonium compounds which are generally incompatible with certain detergent ingredients such as anionic surfactants.

DETAILED DESCRIPTION OF THE INVENTION

The particulate agglomerated carriers of the invention are suitable as additives to or as components of a granular or liquid detergent composition or alternatively they may be used to provide antibacterial effects to washed laundry by adding the agglomerated carrier to the wash solution separately from the detergent composition such as, for example, during the wash cycle or rinse cycle of a washing machine. The agglomerated carrier is comprised of finely divided soil release copolymer having particle sizes in the range of about 150 to 850 microns, which is agglomerated and then size-reduced, if necessary, to particles in the same particle size range of 150 to 850 microns.

The agglomerated carrier is added to the wash solution in an amount to provide a dosage of from about 0.1 to 2 g/liter, preferably 0.5 to 1.0 g/liter.

The soil release polymers useful in the present invention are copolymers of polyethylene terephthalate (PET) and polyoxyethylene terephthalate (POET). They usually will be of molecular weights in the range of about 5,000 to 50,000 preferably in the range of about 9,000 to 20,000 and most preferably about 15,000, according to molecular weight determinations performed on samples thereof that are usually employed herein. Such molecular weights are weight average molecular weights, as distinguished from number average molecular weights, which, in the case of the present polymers, are often lower, In the polymers utilized the polyoxyethylene will usually be of a molecular weight in the range of about 1,000 to 10,000, preferably about 2,500 to 5,000, more preferably 3,000 to 4,000, e.g., 3,400. In such polymers the molar ratio of polyethylene terephthalate to polyoxyethylene terephthalate units (considering

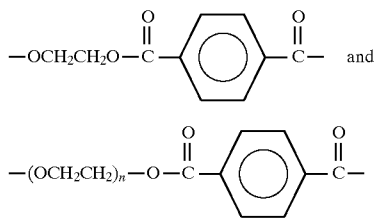

as such units) will be within the range of 2:1 to 6:1, preferably 5:2 to 5:1, more preferably 3:1 to 4:1, e.g., about 3:1. The proportion of ethylene oxide to phthalic moiety in the polymer will normally be at least 10:1 and often will be 20:1 or more, preferably being within the range of 20:1 to 30:1, and more preferably being about 22:1. Thus, it is seen that the polymer may be considered as being essentially a modified ethylene oxide polymer with the phthalic moiety being only a minor component thereof, whether calculated on a molar or weight basis.

Although the described PET-POET copolymer is that which is employed normally by applicants in accordance with the present invention, and that which is highly preferred for its desired functions, other PET-POET polymers, such as those described in U.S. Pat. No. 3,962,152 and British Patent Specification 1,088,984 may also be employed and can be effective soil release promoting agents in the compositions and methods of this invention.

The preparation of the agglomerated carriers of the invention requires that the antibacterial agent be first heated above ambient to its melting point, following which the molten anti-bacterial agent is mixed by conventional means with the particles of soil release polymer to form an agglomerated mixture. The weight ratio of soil release polymer to anti-bacterial agent is generally from about 3:1 to about 1:3 on an active basis and preferably about 1:1. The resultant agglomerated mixture is then conveniently size-reduced manually or in a conventional size-reducing apparatus to produce agglomerated particles having particle sizes in the desired range, generally from about 150 to 850 microns or 20 to 100 mesh (U.S. Sieve).

The agglomerated particles of the invention may also advantageously include a softening ingredient such as a higher fatty acid ester of pentaerythritol, a higher fatty acid ester of pentaerythritol oligomers or a higher fatty acid ester of lower alkylene oxide derivatives of pentaerythritol. Pentaerythritol compound may be abbreviated as PEC herein, which description and abbreviation may apply to any or all of pentaerythritol, oligomers thereof and alkoxylated derivatives thereof, as such, or more preferably and more usually, as the esters, as may be indicated by the context.

The oligomers of pentaerythritol are preferably those of two to five pentaerythritol moieties, more preferably 2 or 3, with such moieties being joined together through etheric bonds. The lower alkylene oxide derivatives thereof are preferably of ethylene oxide or propylene oxide monomers, dimers or polymers, which terminate in hydroxyls and are joined to the pentaerythritol or oligomer of pentaerythritol through etheric linkages. Preferably there will be one to ten alkylene oxide moieties in each such alkylene oxide chain, more preferably 2 to 6, and there will be one to ten such groups on a PEC, depending on the oligomer. At least one of the PEC OH groups and preferably two, are esterified by a higher fatty acid or other higher aliphatic acid, which can be of an odd or even number of carbon atoms.

The higher fatty acid esters of the pentaerythritol compounds are preferably partial esters and more preferably there will be at least two free hydroxyls thereon after esterification (on the pentaerythritol, oligomer or alkoxyalkane groups). Frequently the number of such free hydroxyls is two or about two but sometimes it may be one, as in pentaerythritol tristearate, or as many as eight, as in penta-pentaerythritol tetrapalmitate.

The higher aliphatic or fatty acids that may be employed as esterifying acids are those of carbon atom contents in the range of 8 to 24, preferably 12 to 22 and more preferably 12 to 18, e.g., lauric, myristic, palmitic, oleic, stearic and behenic acids. The fatty acids may be mixtures of such fatty acids, obtained from natural sources, such as tallow or coconut oil, e.g., pentaerythritol ditallowate (the tallow acids diester of pentaerythritol, PEDT) or from such natural materials that have been hydrogenated. Synthetic acids of odd or even numbers of carbon atoms may also be employed. Of the aforementioned fatty acids, lauric, stearic, coco and tallow acids are often preferred (and such preference may depend on the pentaerythritol compound being esterified).

The addition of a PEC compound as described above to the agglomerated carrier of the invention is conveniently carried out by heating the PEC compound to its melting point and then mixing the molten PEC compound with the particles of the invented agglomerated carrier to form a pasty mass which is allowed to dry and then size reduced by conventional means to the desired particle size range.

As noted above, the agglomerated carrier of the invention may be conveniently incorporated in a laundry detergent composition. The active detergent in such a laundry detergent composition is desirably either an anionic surfactant or a nonionic surfactant or a mixture of such surfactants. A mixture of surfactants is often preferred from the standpoint of efficient cleaning.

Any suitable nonionic detergent compound may be used as a surfactant in the present compositions, with many members thereof being described in the various annual issues of *Detergents and Emulsifiers*, by John W. McCutcheon. Such volumes give chemical formulas and trade names for commercial nonionic detergents marketed in the United States, and substantially all of such detergents can be employed in the present compositions. However, it is highly preferred that such nonionic detergent be a condensation product of ethylene oxide and higher fatty alcohol (although instead of the higher fatty alcohol, higher fatty acids and alkyl [octyl, nonyl and isooctyl] phenols may also be employed). The higher fatty moieties, such as the alkyls, of such alcohols and resulting condensation products, will normally be linear, of 10 to 18 carbon atoms, preferably of 10 to 16 carbon atoms, more preferably of 12 to 15 carbon atoms and sometimes most preferably of 12 to 14 carbon atoms. Because such fatty alcohols are normally available commercially only as mixtures, the numbers of carbon atoms given are necessarily averages but in some instances the ranges of numbers of carbon atoms may be actual limits for the alcohols employed and for the corresponding alkyls.

The ethylene oxide (EtO) contents of the nonionic detergents will normally be in the range of 3 to 15 moles of EtO per mole of higher fatty alcohol, although as much as 20 moles of EtO may be present. Preferably such EtO content will be 3 to 10 moles and more preferably it will be 6 to 7 moles, e.g., 6.5 or 7 moles per mole of higher fatty alcohol (and per mole of nonionic detergent). As with the higher fatty alcohol, the polyethoxylate limits given are also limits on the averages of the numbers of EtO groups present in the condensation product. Examples of suitable nonionic detergents include those sold by Shell Chemical Company under the trademark Neodol®, including Neodol 25-7, Neodol 23-6.5 and Neodol 25-3.

Other useful nonionic detergent compounds include the alkylpolyglycoside and alkylpolysaccharide surfactants, which are well known and extensively described in the art.

The preferred alkyl polysaccharides for use herein are alkyl polyglucosides having the formula $$RO(C_nH_{2n}O)_r(Z)_x$$

wherein Z is derived from glucose, R is a hydrophobic group selected from the group consisting of alkyl, alkylphenyl, hydroxyalkylphenyl, and mixtures thereof in which said alkyl groups contain from about 10 to 18, preferably from about 12 to about 14 carbon atoms; n is 2 or 3 preferably, 2; r is from 0 to 10, preferably 0; and x is from 1.5 to 8, preferably from 1.5 to 4, most preferably from 1.6 to 2.7. To prepare these compounds, a long chain alcohol ($R_2OH$ where $R_2$ is an alkyl group of about $C_{10}$ to $C_{18}$) can be reacted with glucose, in the presence of an acid catalyst to form the desired glucoside. Alternatively, the alkyl polyglucosides can be prepared by a two step procedure in which a short chain alcohol ($R_1OH$ wherein $R_1$ is an alkyl having from 1 to 6 carbon atoms) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucoside content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The term "alkyl polysaccharide surfactant", is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is Glucopon 625 CSUP glycoside manufactured by the Henkel Corporation of Ambler, Pa. Glucopon 625 CSUP is a nonionic alkyl polyglycoside characterized by the formula:

$$C_nH_{(2n+1)}O(C_6H_{10}O_5)_xH$$

wherein the alkyl chain length distribution is as follows: for n=10 (2%); n=12 (65%); n=14 (21–28%); n=16 (4–8%) and n=18 (0.5%) and x (degree of polymerization)=1.6. Glucopon 625 CSUP has a pH of 11 to 11.5 (10% of Glucopon 625 in distilled water), a specific gravity at 25° C. of 9.1 lbs./gallon; a calculated HLB of 12.1 and a Brookfield viscosity at 35° C., 21 spindle, 5–10 RPM of 3,000 to 7,000 cps.

Other useful surfactants for the present invention are amide surfactants of the formula $$\underset{R-C-N-Z}{\overset{O\quad R_1}{\underset{\|\quad |}{}}} \quad (a)$$

wherein $R_1$ is H, $C_1$–$C_8$ hydrocarbyl, 2-hydroxyethyl, 2-hydroxypropyl, or a mixture thereof, $R_1$ is preferably methyl; R is $C_7$–$C_{21}$ hydrocarbyl, preferably a straight chain alkyl of $C_9$–$C_{19}$, most preferably a straight alkyl of $C_{10}$–$C_{16}$; and Z is a polyhydroxy hydrocarbyl unit having a linear chain with at least two hydroxyls directly connected to the chain. Preferred polyhydroxy hydrocarbyl groups are derived from a reducing sugar in a reductive amination reaction. Z is most preferably a glycityl group. Suitable reducing sugars include glucose, fructose, maltose, lactose, galactose, mannose, and xylose, as well as glyceraldehyde or mixtures thereof An especially preferred glycityl group is where Z is —$CH_2$—$(CHOH)_4$—$CH_2OH$.

Alternatively, the amide surfactants may comprise amides of the formula $$\underset{R-C-N-Z}{\overset{O\quad R_1-O-R_2}{\underset{\|\quad |}{}}} \quad (b)$$

wherein R is a $C_7$–$C_{21}$ hydrocarbyl group, $R_1$ is a $C_2$–$C_8$ hydrocarbyl group, $R_2$ is a $C_1$–$C_8$ hydrocarbyl or oxy-hydrocarbyl group, and Z is a Polyhydroxy hydrocarbyl unit having a linear chain with at least two hydroxyls directly connected to the chain. Preferred polyhydroxy hydrocarbyl groups are derived from a reducing sugar in a reductive amination reaction. Z is most preferably a glycityl group; the glycityl group —$CH_2$—$(CHOH)_4$—$CH_2OH$ being especially preferred.

Among the anionic surface active agents useful in the present invention are those surface active compounds which contain an organic hydrophobic group containing from about 8 to 26 carbon atoms and preferably from about 10 to 18 carbon atoms in their molecular structure and at least one water-solubilizing group selected from the group of sulfonate, sulfate, carboxylate, phosphorate and phosphate so as to form a water-soluble detergent.

Examples of suitable anionic detergents include soaps, such as, the water-soluble salts (e.g., the sodium potassium, ammonium and alkanol-ammonium salts) of higher fatty acids or resin salts containing from about 8 to 20 carbon atoms and preferably 10 to 18 carbon atoms. Particularly useful are the sodium and potassium salts of the fatty acid mixtures derived from coconut oil and tallow, for example, sodium coconut soap and potassium tallow soap.

The anionic class of detergents also includes the water-soluble sulfated and sulfonated detergents having an aliphatic, preferably an alkyl radical containing from about 8 to 26, and preferably from about 12 to 22 carbon atoms. Examples of the sulfonated anionic detergents are the higher alkyl aromatic sulfonates such as the higher alkyl benzene sulfonates containing from about 10 to 16 carbon atoms in the higher alkyl group in a straight or branched chain, such as, for example, the sodium, potassium and ammonium salts of higher alkyl benzene sulfonates, higher alkyl toluene sulfonates and higher alkyl phenol sulfonates.

Other suitable anionic detergents are the olefin sulfonates including long chain alkene sulfonates, long chain hydroxyalkane sulfonates or mixtures of alkene sulfonates and hydroxyalkane sulfonates. The olefin sulfonate detergents may be prepared in a conventional manner by the reaction of $SO_3$ with long chain olefins containing from about 8 to 25, and preferably from about 12 to 21 carbon atoms, such olefins having the formula $RCH=CHR_1$ wherein R is a higher alkyl group of from about 6 to 23 carbons and $R_1$ is an alkyl group containing from about 1 to 17 carbon atoms, or hydrogen to form a mixture of sultones and alkene sulfonic acids which is then treated to convert the sultones to sulfonates. Other examples of sulfate or sulfonate detergents are paraffin sulfonates containing from about 10 to 20 carbon atoms, and preferably from about 15 to 20 carbon atoms. The primary paraffin sulfonates are made by reacting long chain alpha olefins and bisulfites.

Other suitable anionic detergents are sulfated ethoxylated higher fatty alcohols of the formula $RO(C_2H_4O)_mSO_3M$, wherein R is a fatty alkyl of from 10 to 18 carbon atoms, m is from 2 to 6 (preferably having a value from about 1/5 to 1/2 the number of carbon atoms in R) and M is a solubilizing salt-forming cation, such as an alkali metal, ammonium, lower alkylamino or lower alkanolamino, or a higher alkyl benzene sulfonate wherein the higher alkyl is of 10 to 15 carbon atoms. The proportion of ethylene oxide in the polyethoxylated higher alkanol sulfate is preferably 2 to 5 moles of ethylene oxide groups per mole of anionic detergent, with three moles being most preferred, especially when the higher alkanol is of 11 to 15 carbon atoms. A preferred polyethoxylated alcohol sulfate detergent is marketed by Shell Chemical Company as Neodol 25-3S.

The most highly preferred water-soluble anionic detergent compounds are the ammonium and substituted ammonium (such as mono, di and tri ethanolamine), alkali metal (such as, sodium and potassium) and alkaline earth metal (such as, calcium and magnesium) salts of the higher alkyl benzene sulfonates, olefine sulfonates and higher alkyl sulfates. Among the above-listed anionics, the most preferred are the sodium linear alkyl benzene sulfonates (LABS), and especially those wherein the alkyl group is a straight chain alkyl radical of 12 or 13 carbon atoms.

Amphoteric or ampholytic detergents may be used, if desired, to supplement the anionic and/or nonionic detergent in the composition of the invention. Ampholytic detergents are well known in the art and many operable detergents of this class are disclosed by A. M. Schwartz, J. W. Perry and J. Berch in "Surface Active Agents and Detergents," Interscience Publishers, N.Y., 1958, Vol. 2.

A preferred amphoteric surfactant is of the formula

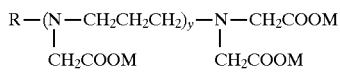

wherein R is an aliphatic hydrocarbonyl, preferably fatty alkyl or fatty alkylene, of 16 to 18 carbon atoms, M is alkali metal, and y is 3 to 4. More preferably R is tallowalkyl (which is a mixture of stearyl, palmityl and oleyl in the proportions in which they occur in tallow), M is sodium and y is about 3.5, representing a mixture of about equal parts of the amphoteric surfactant wherein y is 3 and such amphoteric surfactant wherein y is 4. Among the more preferred amphoteric surfactants of this type is that available commercially under the trade name AmpholakTM™7TX, which is obtainable from Kenobel AB, a unit of Nobel Industries, Sweden.

Builder materials may advantageously be included in the present compositions and may comprise any suitable water soluble or water insoluble builder, either inorganic or organic, providing that it is useful as a builder for the particular nonionic or anionic detergent compounds that may be employed. Such builders are well known to those of skill in the detergent art and include: alkali metal phosphates, such as alkali metal polyphosphates and pyrophosphates, including alkali metal tripolyphosphates; alkali metal silicates, including those of $Na_2O:SiO_2$ ratio in the range of 1:1.6 to 1:3.0, preferably 1:2.0 to 1:2.8, and more preferably 1:2.35 or 1:2.4; alkali metal carbonates; alkali metal bicarbonates; alkali metal sesquicarbonates (which may be considered to be a mixture of alkali metal carbonates and alkali metal bicarbonates); alkali metal borates, e.g., borox; alkali metal citrates; alkali metal gluconates; alkali metal nitrilotriacetates; zeolites, preferably hydrated zeolites, such as hydrated Zeolite A, Zeolite X and Zeolite Y; and mixtures of individual builders within one or more of such types of builders. Preferably the builders will be sodium salts and will also be inorganic. A highly preferred non-phosphate mixed water soluble and water insoluble builder composition comprises carbonate, bicarbonate and zeolite builders. Phosphate-containing builder systems will usually be based on alkali metal (sodium) tripolyphosphate and silicate builders, with such silicate being in relatively minor proportion.

Zeolite A-type aluminosilicate builder, usually hydrated, with about 15 to 25% of water of hydration is particularly advantageous for the present invention. Hydrated zeolites X and Y may be useful too, as may be naturally occurring zeolites that can act as detergent builders. Of the various zeolite A products, zeolite 4A, a type of zeolite molecule wherein the pore size is about 4 Angstroms, is often preferred. This type of zeolite is well known in the art and methods for its manufacture are described in the art such as in U.S. Pat. No. 3,114,603.

The zeolite builders are generally of the formula

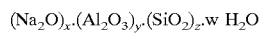

wherein x is 1, y is from 0.8 to 1.2, preferably about 1, z is from 1.5 to 3.5, preferably 2 or 3 or about 2, and w is from 0 to 9, preferably 2.5 to 6. The crystalline types of zeolite which may be employed herein include those described in "Zeolite Molecular Series" by Donald Breck, published in 1974 by John Wiley & Sons, typical commercially available zeolites being listed in Table 9.6 at pages 747–749 of the text, such Table being incorporated herein by reference.

The zeolite builder should be a univalent cation exchanging zeolite, i.e., it should be aluminosilicate of a univalent cation such as sodium, potassium, lithium (when practicable) or other alkali metal, or ammonium. A zeolite having an alkali metal cation, especially sodium, is most preferred, as is indicated in the formula shown above. The zeolites employed may be characterized as having a high exchange capacity for calcium ion, which is normally from about 200 to 400 or more milligram equivalents of calcium carbonate hardness per gram of the aluminosilicate, preferably 250 to 350 mg. eg./g., on an anhydrous zeolite basis.

Other components may be present in the detergent compositions to improve the properties and in some cases, to act as diluents or fillers. Among the suitable fillers, the most preferred is sodium sulfate. Illustrative of suitable adjuvants are enzymes to promote cleaning of certain hard to remove stains from laundry or hard surfaces. Among enzymes, the proteolytic, amylolytic and lipase enzymes are most useful. Other useful adjuvants are foaming agents, such as lauric myristic diethanolamide, when foam is desired, and antifoams, when desired, such as dimethyl silicone fluids. Also useful are bleaches, such as sodium perborate, which may be accompanied by suitable activator(s) to promote bleaching actions in warm or cold water. Flow promoting agents, such as hydrated synthetic calcium silicate, which is sold under the trademark Microcel® C, may be employed in relatively small proportions. Other adjuvants usually present in detergent compositions include fluorescent brighteners, such as stilbene brighteners, colorants such as dyes and pigments and perfume.

The detergent compositions useful in combination with the present invention may be in liquid or in granular form. The liquid carrier for the liquid compositions of this invention is preferably water alone, but an aqueous carrier containing minor amounts of a lower alcohol, such as ethanol or isopropanol, may also be used in some cases. Generally, water levels may be up to about 90% by weight of the composition, for example, from about 20% to about 90%, preferably from about 20% to 70%, by weight. The water may be deionized, but usually tap water is sufficient.

The viscosity of the liquid detergent composition is normally in the range of about 800 to 10,000 centipoises, preferably 2,000–7,000 centipoises, but products of other suitable viscosities may also be useful. At the viscosities mentioned, the liquid detergent is pourable, stable, nonseparating and uniform.

Powder or granular forms of the detergent composition may be prepared by conventional granulation techniques, such as spray drying, wherein a liquid formulation (crutcher slurry) is spray dried and the resulting granular product collected. The crutcher slurry also preferably will contain one or a mixture of granulation aids such as sodium sulfate, silicates, clays and other well known material as such as disclosed in U.S. Pat. Nos. 5,024,778 and 5,332,513. The amount of such granulation aids will generally range from about 10 to 50 wt %. The water content of such granular detergents generally ranges from about 5 to 15 wt %.

EXAMPLE 1

Preparation of Agglomerated Carrier

Agglomerated carrier particles in accordance with the invention were prepared as follows using PCMX as the antibacterial agent and SRP-3 soil release polymer marketed by Rhone-Poulenc.

SRP-3 is composed in part of a polymer referred to as QCF which is a PET-POET copolymer with a molecular weight in the range of about 15,000 to 50,000, but more usually in the preferred range of about 19,000 to 43,000. The mole ratio of polyethylene terephthalate to polyoxyethylene terephthalate units is about 3:1. SRP-3 is a mixture of 50% QCF and 50% sodium sulfate, and is therefore 50% active.

Into a 100 ml glass beaker there was added 25 g of PCMX in solid granular form. The beaker was heated using a hot plate until the PCMX was melted and in liquid form. Forty grams of powdered SRP-3 having a particle size range of from about 150 microns to 850 microns in diameter was introduced into a 1,500 ml glass beaker. Twenty grams of melted PCMX was then poured onto the SRP-3 copolymer, and a large spatula was used to manually mix the two components. The weight ratio of SRP-3:PCMX was 2:1.

The 1,500 ml beaker was then placed in a microwave oven for intervals of 1–2 minutes for drying. After each drying interval, the beaker was removed from the microwave oven and allowed to cool for a period of about 5 minutes during which time the agglomerated mixture was thoroughly mixed using a spatula. Drying was carried out in this manner in the microwave oven for a total drying time of about 45 minutes. The dried mixture was then ground in a mortar and pestle to produce a PCMX/SRP-3 agglomerate having a particle size of below about 850 microns. These agglomerate particles were used in detergent composition (3) described in Example 2.

EXAMPLE 2

To evaluate the antibacterial effects provided to laundered fabrics in accordance with the present invention fabrics were washed in a Maytag washing machine using the protocol described below.

Washing Protocol

Tests were conducted at a water temperature of 77° F.; a water hardness of 150 ppm; a water volume of 45 liters (12 gallons), and a detergent concentration of 7.0 g/liter. For each of three comparative tests, 315 grams of powdered laundry detergent was used (7.0 g/l×45 liters=315 g) and to provide 1% of PCMX in the product formula using an agglomerate in accordance with the invention, 9.5 grams of the PCMX/SRP-3 carrier described in Example 1 was added and mixed with the 315 grams of powdered detergent.

The fabric load consisted of 10"×10" fabric swatches of the following four fabrics: cotton percale; 65% Dacron/35% Cotton; Dacron Single Knit; and Terry Cotton. The total weight of these swatches per washing load was about ½ lb.

The washing was conducted as follows: after filling the washer with water, the detergent product was added and agitated for 2 minutes, following which the swatches were added and washed for 10 minutes. About 500 ml of the wash solution was then taken as a sample for analysis of the level of PCMX. The washing machine was then allowed to drain and continue through the rest of the spin cycle, rinse cycle and final spin cycle.

Two replicates of each fabric were dried in an electric clothes dryer for 45 minutes, or line-dried until dry.

Three detergent compositions were tested as defined below:

(1) Control A; (2) Control A with 1% PCMX; (3) Control A with 1% PCMX/SRP-3 agglomerate. Detergent compositions (1) and (2) are outside the invention; detergent composition (3) is in accordance with the invention.

Control A is a commercial powder detergent having the following composition.

| Control A | |
|---|---|
| Component | Weight Percent |
| Water | 15.1 |
| Dodecyl benzene sulfonate (linear) | 24.3 |
| Silicate (1:2.35) | 10.4 |
| Pentasodium tripolyphosphate | 12.2 |
| Soda Ash | 4.9 |
| Anhydrous sodium sulfate | 29.2 |
| Sodium polyacrylate | 2.2 |
| Enzyme | 0.7 |
| Adjuvants (color, perfume, etc.) | Balance |
| Total | 100.0 |

Detergent composition (2) was prepared by adding PCMX powder to Control A in an amount to provide 1% by weight.

Detergent composition (3) was prepared by adding 9.5 grams of the PCMX/SRP-3 agglomerated carrier described in Example 1 to 315 grams of powdered Control A thereby providing 1% of PCMX and 2% SRP-3 in the final composition.

Protocol for Measurement of PCMX on Fabric

The level of deposition of PCMX antibacterial agent on cotton percale, cotton terry; and Dacron Single Knit fabrics was measured using an HPLC analyzer (High Performance Liquid Chromatography).

The PCMX was extracted from the fabric swatches by first placing small pieces of fabric cut from an initial piece of fabric of about 3"×4" into a 250 ml beaker, followed by the addition of 80 ml of acetonitrile. The beaker was stirred for about 10 minutes and the pieces of fabric were then removed from the beaker. The solution in the beaker was allowed to evaporate to about 5 ml.

The solution was then transferred to a 10 ml volumetric flask. The 250 ml beaker was rinsed with two 1 ml portions of acetonitrile and the acetonitrile was then added to the 10 ml flask. The flask was brought to 10 ml volume with deionized water, and the sample was ready for analysis by HPLC.

The measurements are shown in Tables 1 and 2 below.

TABLE 1

PCMX Antibacterial Agent Deposition on Line-Dried Fabrics

| Detergent Composition | Cotton Terry | Cotton Percale | Dacron Single Knit |
|---|---|---|---|
| (1) Control A | 0 ppm | 0 ppm | 0 ppm |
| (2) Control A with 1% PCMX | 71.5 | 70.0 | 7 |
| (3) Control A with PCMX/SRP-3 Agglomerate (1% PCMX, 2% SRP-3) | 116 | 75.5 | 15.5 |

TABLE 2

PCMX Antibacterial Agent Deposition on Dryer-Dried Fabrics

| Detergent Composition | Cotton Terry | Cotton Percale | 65/35 Dacron/Cotton |
|---|---|---|---|
| (1) Control A | 0 ppm | 0 ppm | 0 ppm |
| (2) Control A with 1% PCMX | 0 | 9.5 | 9.2 |
| (3) Control A with PCMX/SRP-3 Agglomerate (1% PCMX, 2% SRP-3) | 73.8 | 51.8 | 33.3 |

As noted in Tables 1 and 2, laundering of fabrics with detergent composition (3) (a composition in accordance with the invention) resulted in significantly enhanced deposition of PCMX antibacterial agent on the laundered fabrics.

Protocol for Measurement of PCMX in the Wash Solution

After washing the stained fabric swatches for 10 minutes with each of the three detergent compositions described in the washing protocol, a sample of the wash solution was taken for analysis of the level of PCMX.

To 12 ml of the wash solution there was added 12 ml of acetonitrile in a 25 ml flask. The level of PCMX was measured using an HPLC analyzer.

The measurements are shown in Table 3 below:

TABLE 3

PCMX Antibacterial Agent Concentration in the Wash Solutions

| Detergent Composition | PCMX Concentration |
|---|---|
| (1) Control A | 0 ppm |
| (2) Control A with 1% PCMX | 14.5 |
| (3) Control A with PCMX/SRP-3 Agglomerate (1% PCMX, 2% SRP-3) | 36.2 |

As noted in Table 3, the incorporation of the agglomerated carrier of the invention in Composition (3) resulted in significantly higher concentrations of PCMX antibacterial agent in the wash solution media.

What is claimed is:

1. A particulate agglomerated carrier which is an agglomerate of (i) a soil release copolymer of polyethylene terephthalate (PET) and polyoxyethylene terephthalate (POET); and (ii) an antibacterial agent, which carrier is suitable for use in admixture with a laundry detergent composition or as an additive to a wash solution separate from any detergent composition, and which carrier is capable of depositing an effective amount of said antibacterial agent on laundered fabrics, said carrier being comprised of:

(a) particles of said soil release copolymer; and
   (b) an antibacterial agent which is normally solid at ambient temperature, wherein said particles of soil release copolymer are agglomerated at a temperature above ambient with a melt of said antibacterial agent to form an agglomerated mixture which is reduced in size to the range of particle size desired for said particulate carrier.

2. A particulate agglomerated carrier in accordance with claim 1 wherein said soil release copolymer has a molecular weight in the range of about 15,000 to 50,000.

3. A particulate agglomerated carrier in accordance with claim 2 where the molar ratio of the polyethylene terephthalate units (PET) to the polyoxyethylene terephthalate units (POET) in said soil release copolymer is from about 2:1 to 6:1.

4. A particulate agglomerated carrier in accordance with claim 2 wherein the molecular weight of said copolymer is in the range of about 9,000 to 20,000.

5. A particulate agglomerated carrier in accordance with claim 1 wherein the weight ratio of soil release copolymer to antibacterial agent is from about 3:1 to about 1:3.

6. A particulate agglomerated carrier in accordance with claim 1 wherein the antibacterial agent is PCMX (para chloro meta xylenol).

7. A particulate agglomerated carrier in accordance with claim 1 wherein the antibacterial agent is Triclosan (2,4,4' trichloro-2' hydroxydiphenyl ether).

8. A particulate agglomerated carrier in accordance with claim 1 wherein said antibacterial agent does not include a metal ion or alkali metal ion.

9. A particulate agglomerated carrier in accordance with claim 1 which further includes a higher aliphatic $C_{12}$–$C_{22}$ ester of pentaerythritol or a higher $C_{12}$–$C_{22}$ ester of an oligomer of pentaerythritol.

10. A process for depositing an effective amount of an antibacterial agent on laundered fabrics comprising (a) dispersing an effective amount of the particulate agglomerated carrier defined in claim 1 in the wash water or rinse water of a washing machine or hand washing operation; and
   (b) contacting the fabrics to be laundered with said particulate agglomerated carrier in the wash water or rinse water whereby at least a partial amount of the antibacterial agent in said carrier is deposited on the laundered fabrics.

11. A process in accordance with claim 10 wherein the weight ratio of soil release copolymer to antibacterial agent is from about 3:1 to about 1:3.

12. A process in accordance with claim 11 wherein the weight ratio of soil release copolymer to antibacterial agent is about 1:1.

13. A process in accordance with claim 10 wherein the antibacterial agent is PCMX (para chloro meta xylenol).

14. A laundry detergent composition comprising (a) at least one surfactant selected from the group consisting of anionic and nonionic surfactants; and
   (b) a particulate agglomerated carrier in accordance with claim 1.

15. A laundry detergent composition in accordance with claim 14 wherein the weight ratio of soil release copolymer to antibacterial agent in the agglomerated carrier is from about 15:1 to about 5:1.

16. A laundry detergent composition in accordance with claim 14 wherein the molecular weight of the soil release copolymer of PET and POET is in the range of about 9,000 to 20,000.

* * * * *